CHRYSANTHEMUM PLANT
Filed Jan. 24. 1973 2 Sheets-Sheet 1
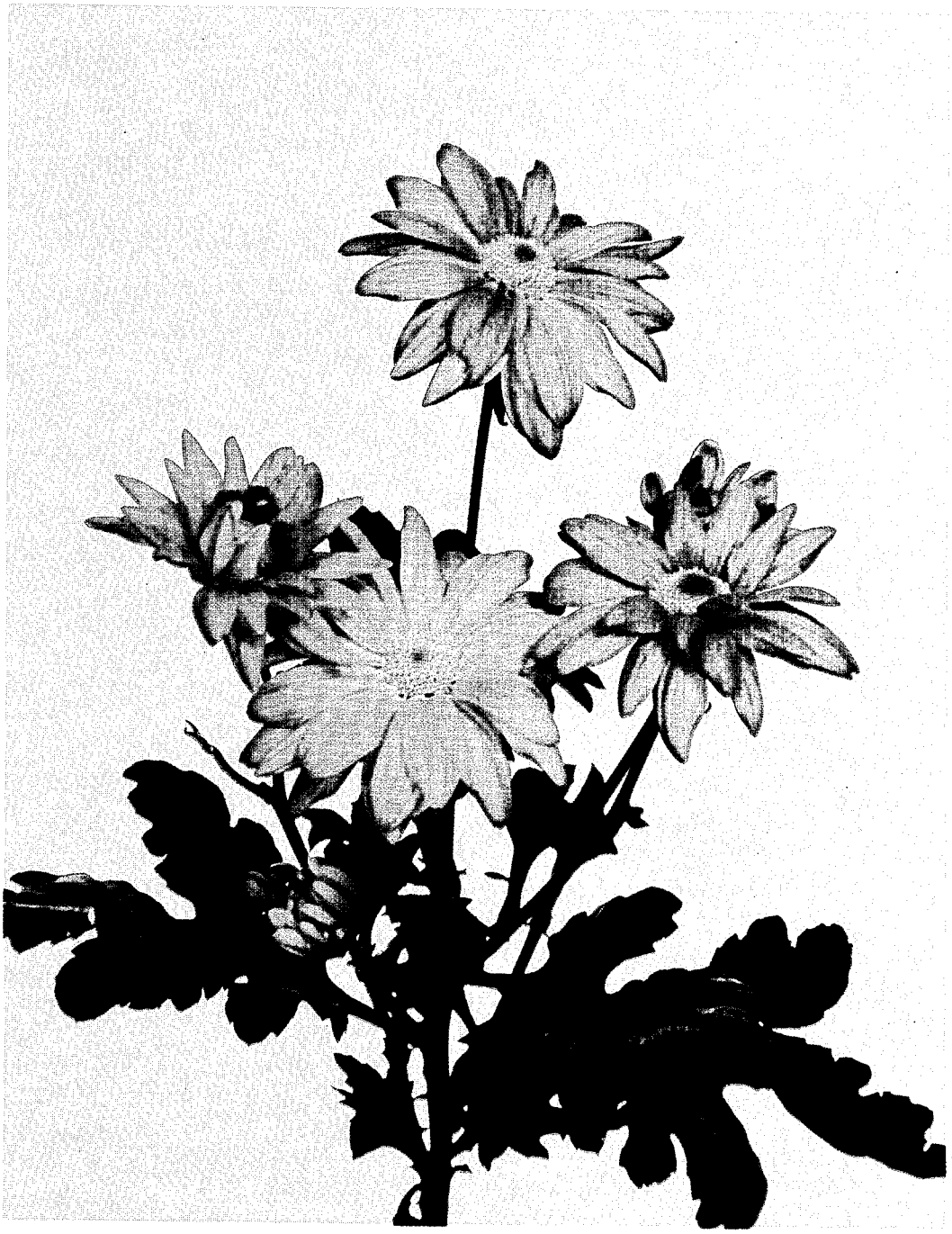

CHRYSANTHEMUM PLANT
Filed Jan. 24, 1973 2 Sheets-Sheet 2
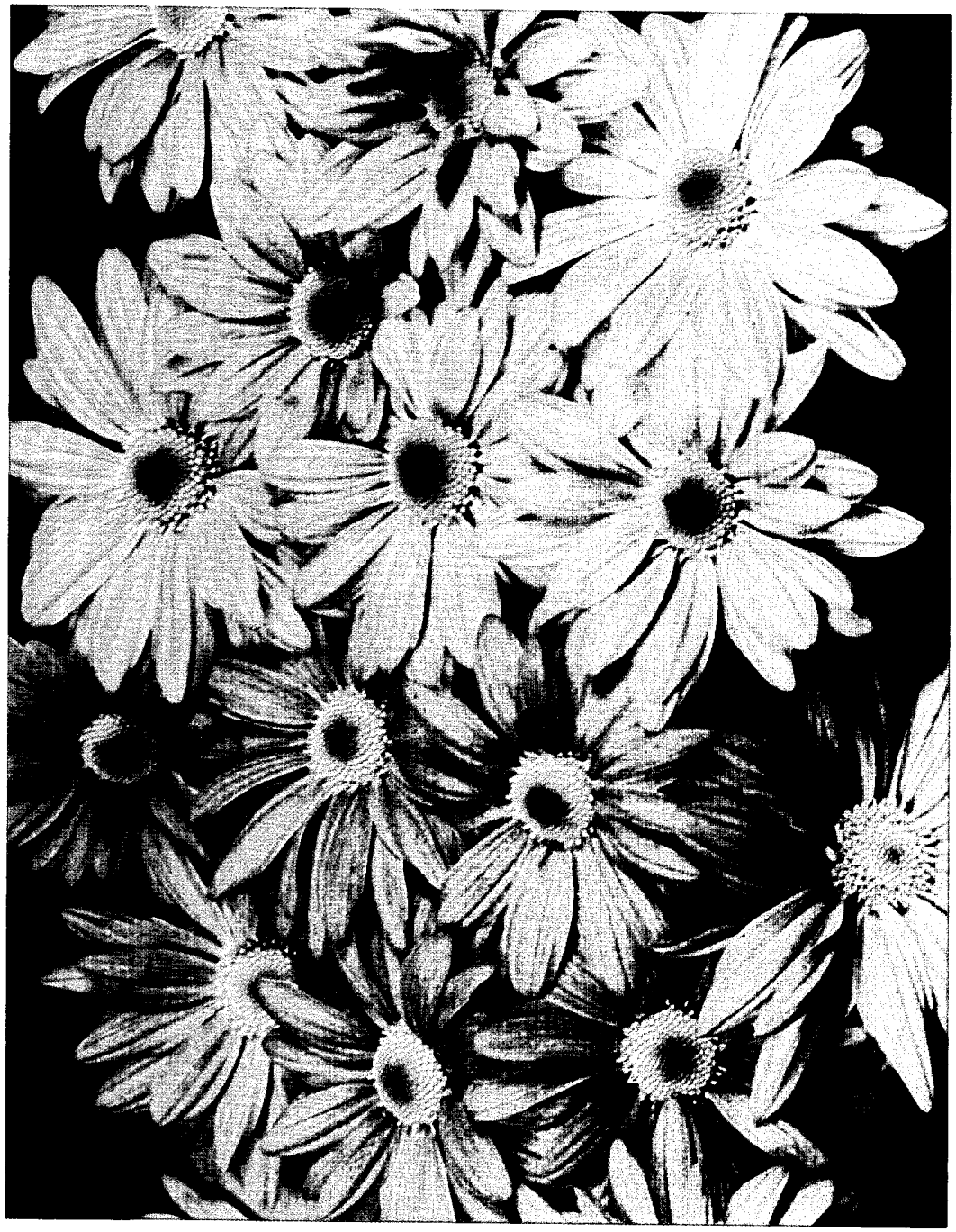

United States Patent Office

Plant Pat. 3,604

Patented Sept. 3, 1974

3,604
CHRYSANTHEMUM PLANT

Leonard E. Carrier, 1911 Sheridan Road, Encinitas, Calif. 92024, and Walter H. Jessel, Jr., Doylestown, and William E. Duffett, Akron, Ohio; said Jessel and Duffett assignors to said Carrier

Filed Jan. 24, 1973, Ser. No. 326,540

Int. Cl. A01h *5/00*

U.S. Cl. Plt.—74 1 Claim

The present invention comprises a new and distinct cultivar of chrysanthemum plant of daisy form known by the varietal name Tuneup, which is a sport of the unpatented cultivar known in the United States as Tuneful.

The new cultivar is similar in many respects to the unpatented cultivar Deep Tuneful, also a sport of Tuneful, the new cultivar having the same characteristics as Deep Tuneful in respect to:

1. Flower form.
2. Foliage size, shape and color.
3. Recommended period of value.
4. Intolerance of high temperatures for bud development.

The new cultivar is distinguished from Deep Tuneful by the following characteristics when grown under comparable conditions:

1. An intense red-bronze flower color. Deep Tuneful is a dark orange-bronze.
2. Flowers approximately ¼" to ½" larger in diameter.
3. Approximately 2" increased vigor.
4. Approximately two days earlier response.

The new cultivar is also similar in certain respects to the cultivar Red Dazzler, disclosed in pending application Ser. No. 277,866, filed Aug. 4, 1972, in the names of Ralph Bond, Walter H. Jessel, Jr. and William E. Duffett, and the cultivar Aglow, disclosed in U.S. Plant Pat. No. 3,212, issued June 20, 1972, with both of these cultivars also being in the generally bronze family and of daisy form. The new cultivar is distinguished from Red Dazzler by its relative intolerance of high temperatures for bud development, thereby limiting the suggested flowering of the new cultivar in the northern and western United States from May through June and October through November. Red Dazzler, on the other hand, can be flowered in these same areas from April through October. In addition, the shape of the petals differ somewhat, and the new cultivar has a response period of approximately ten weeks as compared to the nine week response period of Red Dazzler. The flower size of Red Dazzler is slightly larger than Tuneup when fully expanded.

With respect to Aglow, the new cultivar has a smaller flower size when fully expanded, an approximately ten weeks response period compared to the approximately nine weeks response period of Aglow, and less vigor and productivity than Aglow. It possesses the same characteristic as Aglow of intolerance to high temperature periods, with the suggested flowering peroid for both cultivars being comparable. The flower color of the new cultivar Tuneup is more reddish in tone than the flower color of Aglow.

The new cultivar was discovered in a cultivated area in Encinitas, California, and has been asexually reproduced by cuttings at Barberton, Ohio. The new cultivar has been found to retain its distinctive characteristics through successive propagations.

The new cultivar when grown in the vicinity of Barberton, Ohio, has a response period of approximately 10 weeks, and the following detailed description is based on observations made of the new cultivar in a greenhouse in Barberton, Ohio. The response time, blooming period, color, and total vigor may vary significantly with varying environmental conditions such as temperature, day length, and light intensity.

Suggested flowering in the northern and western United States is from May through June, and October through November. Suggested flowering in coastal California is from June through November.

In the accompanying photographic drawings, sheet 1 comprises a specimen photograph of the new cultivar, and sheet 2 comprises a color comparison photograph, with the more reddish flowers comprising the new cultivar Tuneup and the more orange flowers comprising the cultivar Deep Tuneful.

In the description which follows, color references are made to the Munsell Color Book, 1963 edition, and comparisons are made with the cultivar Deep Tuneful. Where only a single value or description appears for the new cultivar, the same value applies to the comparison cultivar as well.

Botanical classification: *Chrysanthemum morifolium*

| | Tuneup | Deep tuneful |
|---|---|---|
| Bloom: | | |
| Size | 2½"–3¼" | 2¼"–2¾". |
| Fully expanded | 3¼"–3½" | 3". |
| Borne | Clusters on elongated pedicels | |
| Stems | Strong | |
| Form | Daisy (single) | |
| Permanence | 7–10 days | |
| Color: | | |
| Center of flower | Yellow green, 2.2GY4.3/7.1 | |
| Base of petals | Yellow green, 1.7GY6.2/10.1 | |
| Inside of petals | Red, 9.5R3.0/9.0 over bronze, 3.0YR4.2/10.9 | Orange bronze, 1.9YR3.8/10.5 over yellow, 10Y8.0/11.9. |
| Reverse of petals | Bronze, 8.0YR4.0/8.4 over yellow, 4.8Y8.4/12.5 | Bronze, 4.6YR5.1/12.5 over yellow, 9.8Y8.8/12.8. |
| Tonality from a distance | Red bronze | Orange bronze. |
| Discoloration | Bronze, 8.0YR4.0/8.4 over yellow, 4.8Y8.4/12.5 | Orange bronze, 1.9YR3.8/10.5 over yellow 1.0Y8.0/11.9 . |
| Petals: | | |
| Texture | Smooth | |
| Appearance and form | Open at base, flat multi-ridge tapering to a blunt tip | |
| Arrangement | Composite, whorled on a single receptacle | |
| Persistence | Resists shatter | |
| Fragrance | Typical chrysanthemum | |
| Reproductive organs: | | |
| Stamen, anthers | 200+ | |
| Pollen | Abundant to none (functional sterility) | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright | |
| Height | Approximately 30"–34" when given 2-3 long day weeks and 12-13 weeks total crop time as defined in the time-tables of Yoder Brothers, Inc., Barberton, Ohio, for the various seasons. | Approximately 28"–32" when given 2-3 long day weeks and 12-13 weeks total crop time as defined in the time tables of Yoder Brothers, Inc., Barberton, Ohio, for the various seasons. |
| Spread | None grown single stem to slight when pinched | |

TABLE—Continued

| | Tuneup | Deep tuneful |
|---|---|---|
| Foliage: | | |
| Top side | Very dark green, 8.9GY2.3/4.7 | |
| Size | Length to width ratio: 13.9 with length up to 3¼", and width up to 2¼". | |
| Quantity | Numerous | |
| Shape | Spatulate lobed | |
| Texture | Smooth | |
| Ribs and veins | Prominent | |
| Edge | Moderately indented | |
| Serration | Coarse | |
| Underside | Medium green, 6.1GY3.2/5.8 | |
| Stipules | Very prominent | |

We claim:

1. A new and distinct cultivar of chrysanthemum characterized particularly by its daisy form, intense red-bronze flower color; approximate ten week response period; flower size of 3¼"–3½" when fully expanded; suggested flowering period in the northern and western United States from May through June and October through November, and by its intolerance of high temperatures for bud development.

No references cited.

ROBERT E. BAGWILL, Primary Examiner